United States Patent [19]

Laskowski et al.

[11] Patent Number: 5,056,358
[45] Date of Patent: Oct. 15, 1991

[54] APPARATUS FOR THE DETERMINATION OF RHEOLOGICAL PROPERTIES OF SEDIMENTING SUSPENSIONS

[75] Inventors: Janusz S. Laskowski, Richmond; Bernhard Klein, Vancouver; Susan J. Partridge, Vancouver, all of Canada

[73] Assignee: University of British Columbia, Vancouver, Canada

[21] Appl. No.: 398,184

[22] Filed: Aug. 24, 1989

[30] Foreign Application Priority Data

Aug. 26, 1988 [CA] Canada .................................. 575872

[51] Int. Cl.⁵ .............................................. G01N 11/14
[52] U.S. Cl. ................................................................ 73/6
[58] Field of Search ...................................... 73/60, 59

[56] References Cited

U.S. PATENT DOCUMENTS 4,214,475 7/1980 Carter et al. .......................... 73/59

FOREIGN PATENT DOCUMENTS

| 18742 | 2/1981 | Japan | 73/60 |
| 137306 | 7/1960 | U.S.S.R. | 73/60 |
| 584228 | 12/1977 | U.S.S.R. | 73/59 |
| 586369 | 12/1977 | U.S.S.R. | 73/60 |
| 868474 | 9/1981 | U.S.S.R. | 73/60 |
| 1062566 | 12/1983 | U.S.S.R. | 73/59 |

Primary Examiner—John Chapman
Assistant Examiner—Joseph W. Roskos
Attorney, Agent, or Firm—Seed and Berry

[57] ABSTRACT

This invention relates to an apparatus for determining the rheological properties of sedimenting suspensions. More particularly, this invention relates to a method and apparatus which permits the accurate determination of the rheological properties of particulate suspensions in which the particles are settling. An apparatus for evaluating the rheological properties of sedimenting suspensions comprising: (a) a sedimenting suspension retainer; (b) a device means suspended in the retainer, the retainer and suspended device being capable of being rotated relative to one another, the device being permeable to the passage of particles settling in the sedimenting suspension, the suspended device being suspended in the sedimenting suspension in the retainer in the region having constant density.

15 Claims, 7 Drawing Sheets

APPARATUS FOR THE DETERMINATION OF RHEOLOGICAL PROPERTIES OF SEDIMENTING SUSPENSIONS

FIELD OF THE INVENTION

This invention relates to an apparatus for determining the rheological properties of sedimenting suspensions. More particularly, this invention relates to a method and apparatus which permits the accurate determination of the rheological properties of particulate suspensions in which the particles are settling.

BACKGROUND OF THE INVENTION

The determination of the rheological properties of rapidly sedimenting suspensions is very important in basic research and in many different fields. Examples of materials that are produced, processed or utilized as unstable particulate suspensions include mineral suspensions, coal-water slurries, magnetite dense media, flotation products, drilling muds, foods, agricultural chemicals, sewage, river deposits, and the like. The ease of transportation of such materials and their application to a particular purpose are dependent on the flow and viscous characteristics of the suspension. It is thus essential that the rheological properties of the materials can be accurately determined. This is not an easy task when dealing with materials where the particles are coarse or have a high density, or where the medium viscosity is low. In such materials, rapid sedimentation can occur thereby making it difficult to accurately measure the rheological properties of the materials.

In the mining and mineral processing industry, coal and many minerals are upgraded by means of a dense medium separation process, whereby valuable mineral components are separated from their gangue by virtue of their density difference. The dense medium used is generally a suspension of particles, usually magnetite or ferrosilicon in water, which experiences rapid sedimentation. The efficiency of separation depends on the viscous properties of this suspension, and hence optimization of the process is dependent on being able to accurately determine the rheological properties of the dense medium suspension.

Rotational viscometers have been used for many years to measure the rheological properties of liquids and suspensions. Samples of these materials are contained in the annular gap between coaxial cylinders, where either the cup or bob rotates depending on the system. The resistance to the rotation by the sample is a measure of its viscosity. For increased sensitivity, a double gap concentric cylinder arrangement is used. In both cases, there is just a small space between the bottom of the bob and the cup and between the top of the bob and the top of the cup.

SUMMARY OF THE INVENTION

The invention is directed to a new method and device for the determination of the rheological properties of a sedimenting suspension. The device is a novel concentric cylinder cup and bob fixture and is a modification of those conventionally attached to rheometers. The modifications to the device extend the operating potential of the rheometer to allow for measurements of the rheological properties of quickly sedimenting (unstable) suspensions that exhibit zone settling characteristics. These accurate measurements are achieved by maintaining the measuring component of the device in the constant density zone of the settling suspension.

The invention is directed to an apparatus for evaluating the rheological properties of sedimenting suspensions having a temporary constant density zone comprising: (a) means for retaining a sedimenting suspension; (b) means suspended in said retaining means and said sedimenting suspension, being capable of being rotated relative to one another, said suspended means being permeable to the passage of particles settling in the sedimenting suspension, the suspended means being suspended in the sedimenting suspension in the region having constant density.

The retaining means may be an upright hollow cylinder, closed at the bottom, and being adapted to have the suspended means suspended in the interior thereof through the top region of the cylinder. The suspended means can be in the form of a cylinder which has a diameter less than the diameter of the cylindrical retaining means, the suspended means being suspended in the interior of the cylindrical retaining means in a coaxial relationship with the cylindrical retaining means, the retaining means and the suspended means defining therebetween an annular space.

A hollow cylindrical means of diameter less than the cylindrical suspended means may be positioned within at least a portion of the interior of the cylindrical suspended means, said inner cylinder being permeable to particle transmission at the upper end thereof, and being arranged in coaxial relationship with the cylindrical retaining means and the cylindrical suspended means. A portion of the sidewall of the interior of the cylindrical suspended means, and a portion of the exterior sidewall of the inner cylinder means, form therebetween an annular space.

The cylindrical retaining means may be of sufficient height that a sedimenting suspension placed in the interior of the cylindrical retaining means separates for a time into four zones, an uppermost supernatant zone, a transition zone below the supernatant zone, a constant density zone below the transition zone, and a consolidation zone at the bottom of the sedimenting suspension.

The cylindrical suspended means may be suspended in the constant density zone and rotated relative to the retaining means and the inner cylindrical means. The retaining means and the inner cylindrical mean may be rotated relative to the suspended means.

The cylindrical suspended means may be suspended by a spider and shaft combination, the spider being permeable to passage of particles settling in the sedimenting suspension, and the shaft means serving to rotate the cylindrical suspended means relative to the retaining means. The shaft means may serve to hold the cylindrical suspended means stationary while the retaining means and inner cylinder means are rotated.

The apparatus can be contained in a temperature control medium. The temperature control medium may be a jacket enveloping a major portion of the apparatus and containing water which is maintained at a constant temperature.

The invention is also directed to a method of evaluating the rheological properties of sedimenting suspensions which separate for a period of time into four zones, an uppermost supernatant zone, a transition zone below the supernatant zone, a constant density zone below the transition zone, and a consolidation zone at the bottom of the sedimenting suspension, comprising placing the sedimenting suspension in a retaining means and placing a means in the constant density zone of the suspension, and measuring the rheological properties of the constant density zone by rotating the retaining means and the placed means relative to one another.

DRAWINGS

In drawings which illustrate the prior art, and a specific embodiment of the invention, which should not be regarded as restricting the spirit or scope of the invention in any way:

DETAILED DESCRIPTION OF SPECIFIC EMBODIMENTS OF THE INVENTION

Figure 1:
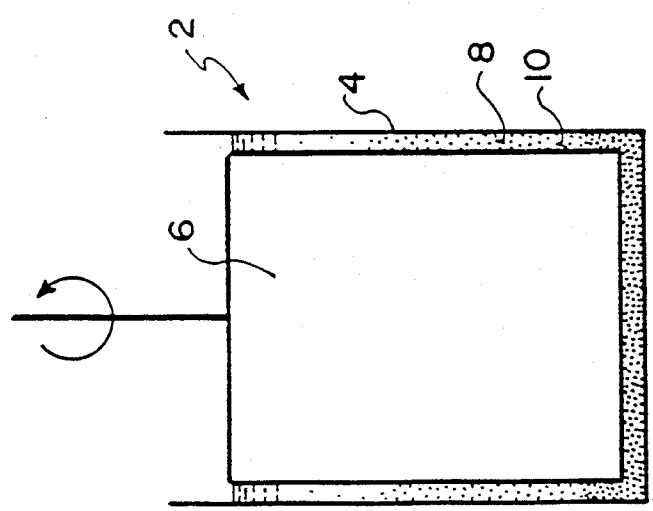
FIG. 1 depicts in side elevation view a schematic representation of a single gap concentric cylinder rotational viscometer fixture.

The rheological properties of liquids and suspensions have been determined by rotational viscometers for many years. FIG. 1 illustrates in side elevation view a schematic representation of a conventional single gap concentric cylinder rotational viscometer fixture 2. The viscometer fixture 2 is constructed of a cup 4, with a cylindrical bob 6 axially suspended in the interior of the cup to provide an annular gap 8 between the exterior surface of the bob 6 and the interior surface of the cup 4. A sample of the material to be analyzed, namely suspension 10, is contained in the annular space 8 between the coaxially arranged cup 4 and bob 6. In use, either the cup 4 or the bob 6 rotates depending on the system utilized. Resistance by the sample to rotation of the cup or bob is a measure of its viscosity.

Figure 2:
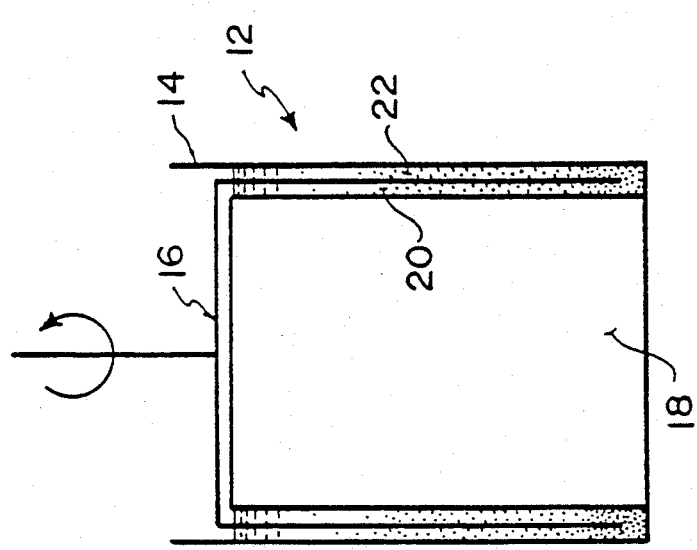
FIG. 2 illustrates in side elevation view a schematic representation of a double gap concentric cylinder rotational viscometer fixture.

FIG. 2 depicts in side elevation view a schematic representation of a conventional double gap concentric cylinder rotational viscometer fixture 12. The viscometer fixture 12 is constructed of a cylindrical cup 14 in which is suspended coaxially a bob 16 which is basically an inverted hollow cup. The bob 16 is coaxially positioned between the cylindrical cup 14 and an inner cylinder 18. This orientation creates an inner annular gap 20 and an annular outer gap 22. The suspension is contained in both the inner and outer annular gaps 20 and 22. The double annular gap concentric cylinder arrangement depicted in FIG. 2 provides increased viscosity measuring sensitivity. With both the single gap and double gap rotational viscometer designs, there is only a small space between the bottom of the bob and the cup in each case. Any collection of settled sediment at the bottom of the cup therefore interferes with an accurate reading of viscosity. In addition, the cup extends only slightly higher than the top of the bob. Any particle depletion of the suspension due to sedimentation at the top of the bob therefore results in inaccurate viscosity measurements.

The above types of arrangements are only suitable for pure liquids and for well dispersed stable suspensions where sedimentation is negligible. However, in the case of many particulate suspensions, particle sedimentation is an inherent property of the system. Sedimentation of particles in the suspension results in a build-up of sludge at the bottom of the cup which impedes the rotation of the bob and gives a falsely high viscosity response. Also, at the top of the cup, a layer of supernatant fluid forms which offers less resistance to the rotating bob than the original suspension, thereby also affecting the viscosity response. The manner in which these two effects influence the net measured viscosity is not precisely known. Obviously, however, it cannot be assumed that one cancels the other.

It is clear that the standard cup and bob arrangement is not suitable for use with unstable sedimenting suspensions. Many inventors have addressed this problem, but none with complete success. The novel invention disclosed herein is a modification of the standard cup and bob arrangement and enables rheological measurements to be made on rapidly settling suspensions.

Figure 3:
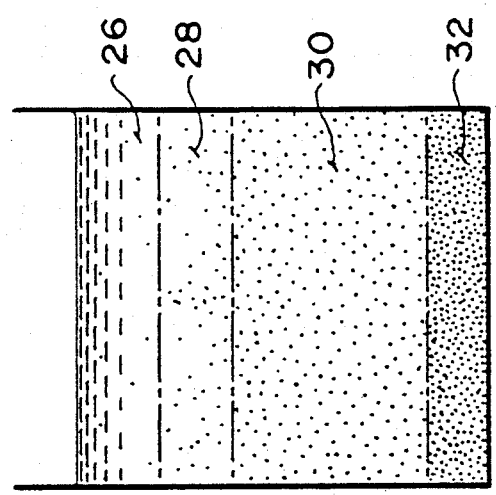
FIG. 3 illustrates in side elevation view a schematic representation of the zone settling characteristics of a particulate suspension.

FIG. 3 illustrates in side elevation view a schematic representation of the zone settling characteristics of a typical dynamic particulate suspension. A column of a suspension which is undergoing sedimentation, as illustrated in FIG. 3, may be characterized by four distinct zones. At the top, there is a supernatant layer 26. Below that there is a transition zone 28. Below that there is a constant density zone 30. Lastly, at the bottom, there is a consolidation zone 32. The supernatant layer 26 consists mostly of liquid and generally has a low viscosity because most of the sedimenting particles have precipitated from this layer. The transition zone 28 is in a dynamic state because particles are still settling out of the transition zone as a function of time. The constant density zone 30, while also in a dynamic state, nevertheless tends to have a reasonably constant density and thus reasonably constant rheological properties. The lowermost consolidation zone 32 contains an over abundance of sedimented particles and as a consequence, the viscosity response in that zone is high relative to the overall viscosity of the suspension.

Figure 4:
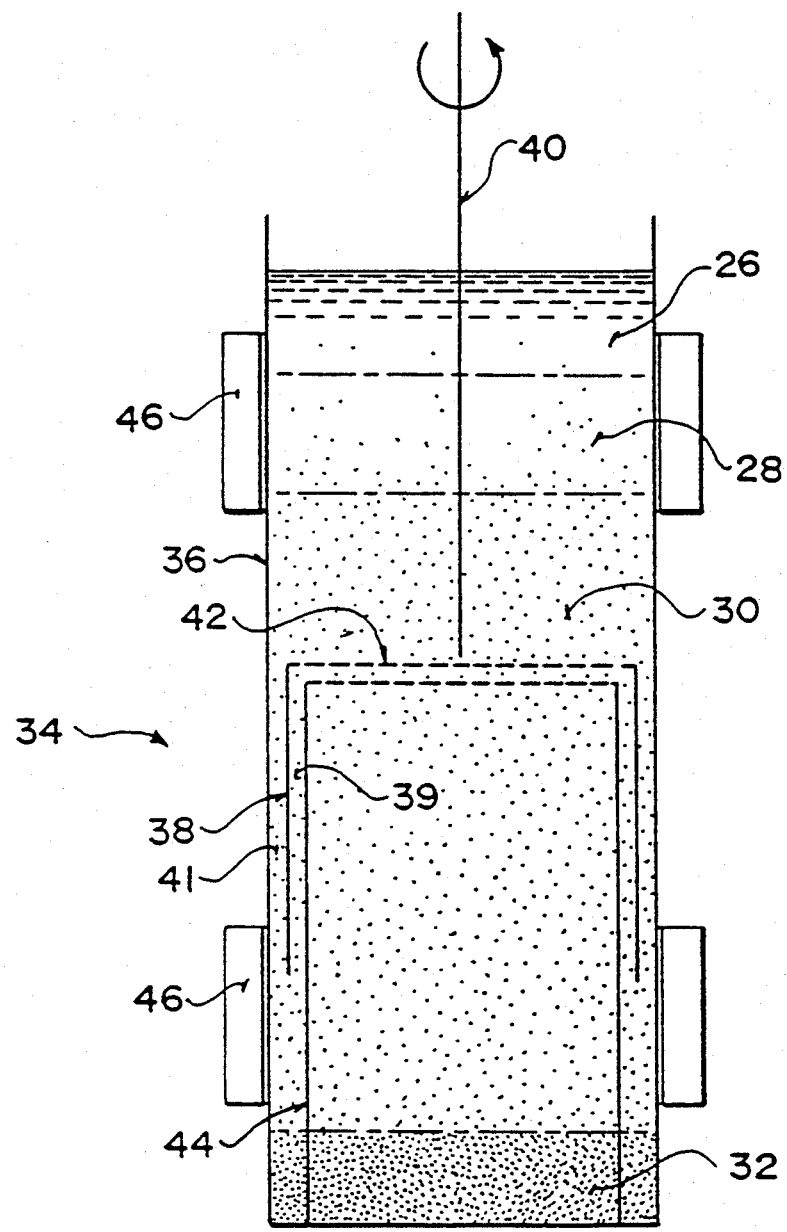
FIG. 4 depicts in side elevation view a schematic representation of an elongated rheometer fixture for determining the viscosity characteristics of sedimenting suspensions.

FIG. 4 depicts in side elevation view a schematic representation of the elongated rheometer fixture 34 according to the invention. The sensing portion of the fixture 34 is maintained in the constant density zone of a typical sedimenting suspension (see FIG. 3) and as a consequence, accurate measurements of the rheological properties of the sedimenting suspension can be obtained utilizing the fixture 34 depicted in FIG. 4.

As seen in FIG. 4, the rheometer fixture 34 is constructed of an elongated upright hollow cylindrical cup 36 which is open at the top and closed at the bottom. The bob 38 is suspended co-axially in the interior of the hollow cylindrical cup 36 by means of an elongated shaft 40, which extends upwardly along the axis of the cup 36. The bob 38 is rotated (see arrow) by means of shaft 40. If desired, the cup 36 can be rotated relative to the bob 38. The bob 38 is constructed in the form of a hollow cylinder, which has a perforated top portion and an open bottom portion. The bob 38 is suspended coaxially so that it surrounds the upper portion of a fixed inner cylinder 44, which rests on the bottom of cup 36. The cylinder 44 has an open top which permits the passage of particles settling from the suspension, and is open at the bottom where it meets the bottom of the cup 36. The cylinder 44 is also disposed co-axially within the interior of the cup 36 and the bob 38, to provide a double annular space 39 and 41 between the coincident walls of the cup 36, the bob 38, and the cylinder 44.

FIG. 4 also illustrates the dispersion of the sedimenting suspension throughout the interior of the cup 36. The supernatant zone 26 is at the top, while the transition zone 28 exists immediately below the supernatant zone 26. The major portion of the distribution of the suspension is taken up by the constant density zone 30. The consolidation zone 32 is at the base of the suspension immediately above the bottom of the cup 36. It is important to note that the bob 38 is suspended by shaft 40 at an appropriate elevation so that it is located entirely in the constant density zone 30, throughout the duration of the measurement, usually 2 to 5 minutes. It is also important to note that the bob 38 is suspended by shaft 40 well above the consolidation zone 32, which consists of a concentration of settled particles. Thus the consolidation zone 32 does not interfere in any way with the rotation of the bob 38. In addition, the bob 38 should be positioned well below the bottom of the transition zone 28 to prevent measurements in a particle depleted zone.

To prevent solids build up, resulting from sedimentation, on the top of the bob 38, the bob 38 is attached to the shaft 40 via a spider 42 which provides a maximum amount of open space for particles to settle freely through. The inner cylinder 44 is hollow and has an open top for the same reason. A support sleeve 46 encircles the cup 36 and supports the rheometer 34 inside the water jacket. The cup 36 is surrounded by a constant temperature water jacket (not shown) for temperature control.

The extent of the constant density zone depends on the height of the sedimenting column and the settling rate of the suspension. Hence the cup 36 has a sufficient height to ensure a substantial constant density zone, for a given suspension, throughout the duration of the experiment. Experiments are usually conducted within two to four minutes. The bob 38 is maintained in the constant density zone 30 for the duration of the measurement. The double gap geometry provides maximum accuracy.

Using this device 34 attached to any conventional rotational viscometer, a complete characterization of the viscous properties of rapidly sedimenting suspensions can be made.

Some of the novel and unusual features of this device are the dimensions of the cup 36 and bob 38 arrangement. These dimensions are set to take advantage of the zone settling characteristics of a suspension. The cup 36 and the shaft 40 attached to the bob 38 are elongated to a sufficient extent that the bob 38 can be positioned at a height in the cup 36 where there is an ample height of constant density zone. Using rheometers with cups and bobs of standard dimensions, it is not possible to perform rheological measurements on rapidly sedimenting suspensions. The apparatus of this invention solves this problem by permitting the measurement of the rheological properties of suspensions of rapidly settling particles.

The method and apparatus described here utilize a rotational viscometer, not a tube viscometer that has the problems of heterogeneous flow, wall effects and plug flow formation. Other adaptations to rotational viscometers result in possible turbulence or undefined shear rates in the sensing area. This new approach has none of these sources of error. The apparatus and method are therefore a novel improvement over existing systems with no obvious limitations.

EXAMPLE

A prototype of the proposed device has been built and tested at The University of British Columbia, Vancouver, Canada. The device built consists of a cylindrical cup of height 25.5 cm and internal diameter 4.1 cm containing an inner cylinder of height 13.5 cm and external diameter of 3.8 cm. A bob of height 6 cm and external diameter 4 cm and inside diameter 3.9 cm is suspended by an elongated shaft of height 15 cm from the drive unit. This bob is positioned coaxially between the inside wall of the cup and the outside wall of the inner cylinder. The device was tested with standard viscosity oils and magnetite particulate suspensions.

Figure 5:
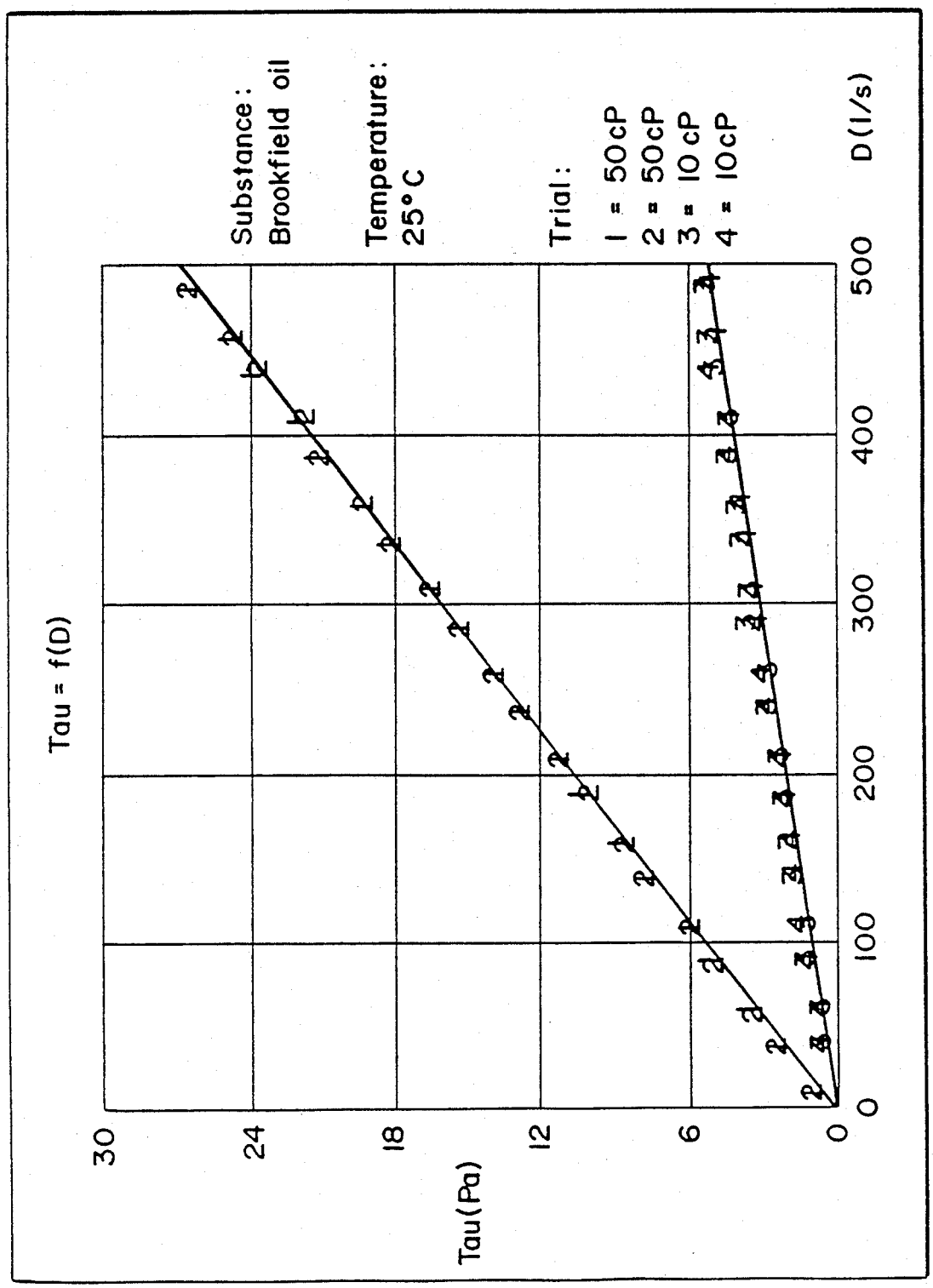
FIG. 5 shows the rheological flow curves generated for various oils.

A Brookfield standard viscosity oil, 50 cP, was used to calibrate the device. This calibration was checked using a Brookfield standard viscosity oil, 10 cP, and the calibration was found to be accurate over the viscosity range tested. FIG. 5 shows the rheological flow curves generated for each of these oils. They can be seen to exhibit the expected Newtonian behaviour. Repeat tests show good agreement.

Figure 6:
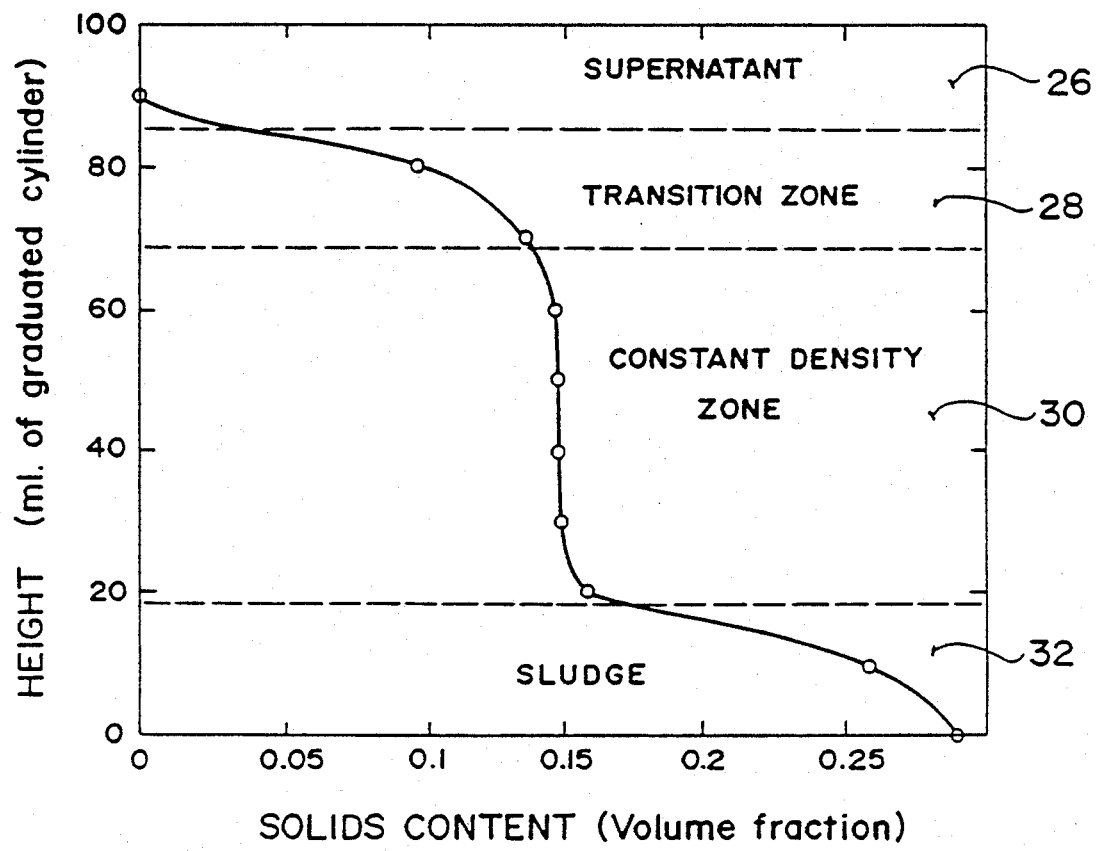
FIG. 6 shows the solids concentration profile of a suspension after three minutes of sedimentation.

Zone settling properties of a magnetite suspension, density 1.6 g/cm$^3$, were determined by sampling the sedimenting suspension in a graduated cylinder at prescribed heights as a function of time. FIG. 6 shows the solids concentration profile of such a suspension after three minutes of sedimentation. The profile clearly shows that magnetite suspensions exhibit zone settling properties with its characteristic supernatant, transition, constant density and consolidation zones. It can also be seen that the constant density zone is of substantial height even after three minutes of settling.

Figure 7:
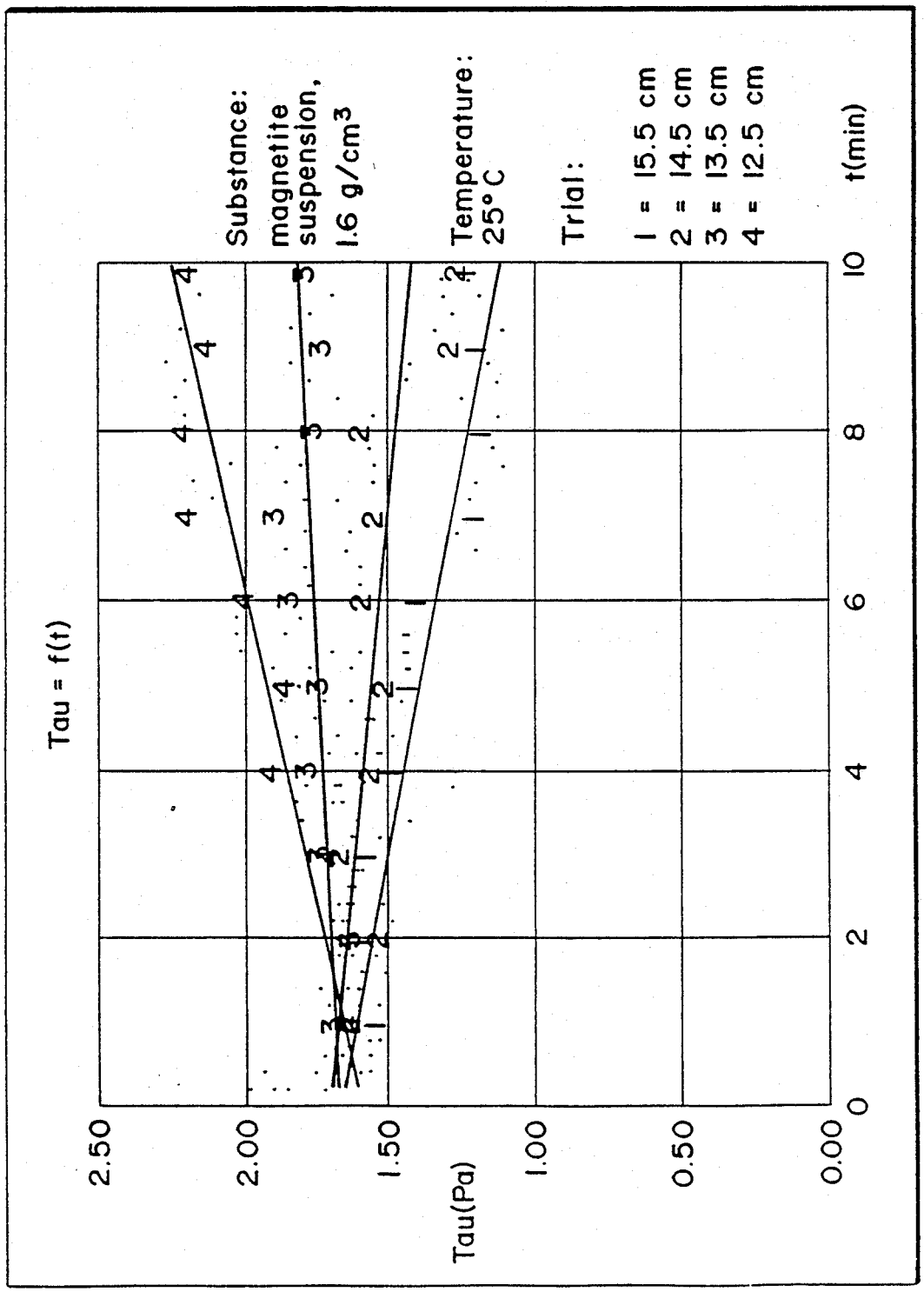
FIG. 7 shows a constant stress measured with time.

In order to establish the best position for the bob in the sedimenting column, the rheometer was used to measure shear stress as a function of time at various heights in the cylinder. A single gap concentric cylinder arrangement with an elongated cup and shaft was used for these tests. FIG. 7 shows that at a height of 13.5 cm, a constant stress was measured with time. At positions above this in the cylinder, the shear stress decreased with time due to the depletion of particles in the region surrounding the bob. At positions below 13.5 cm in the cup, the shear stress increased with time as a result of development of the consolidation zone around the lower portion of the bob.

Figure 8:
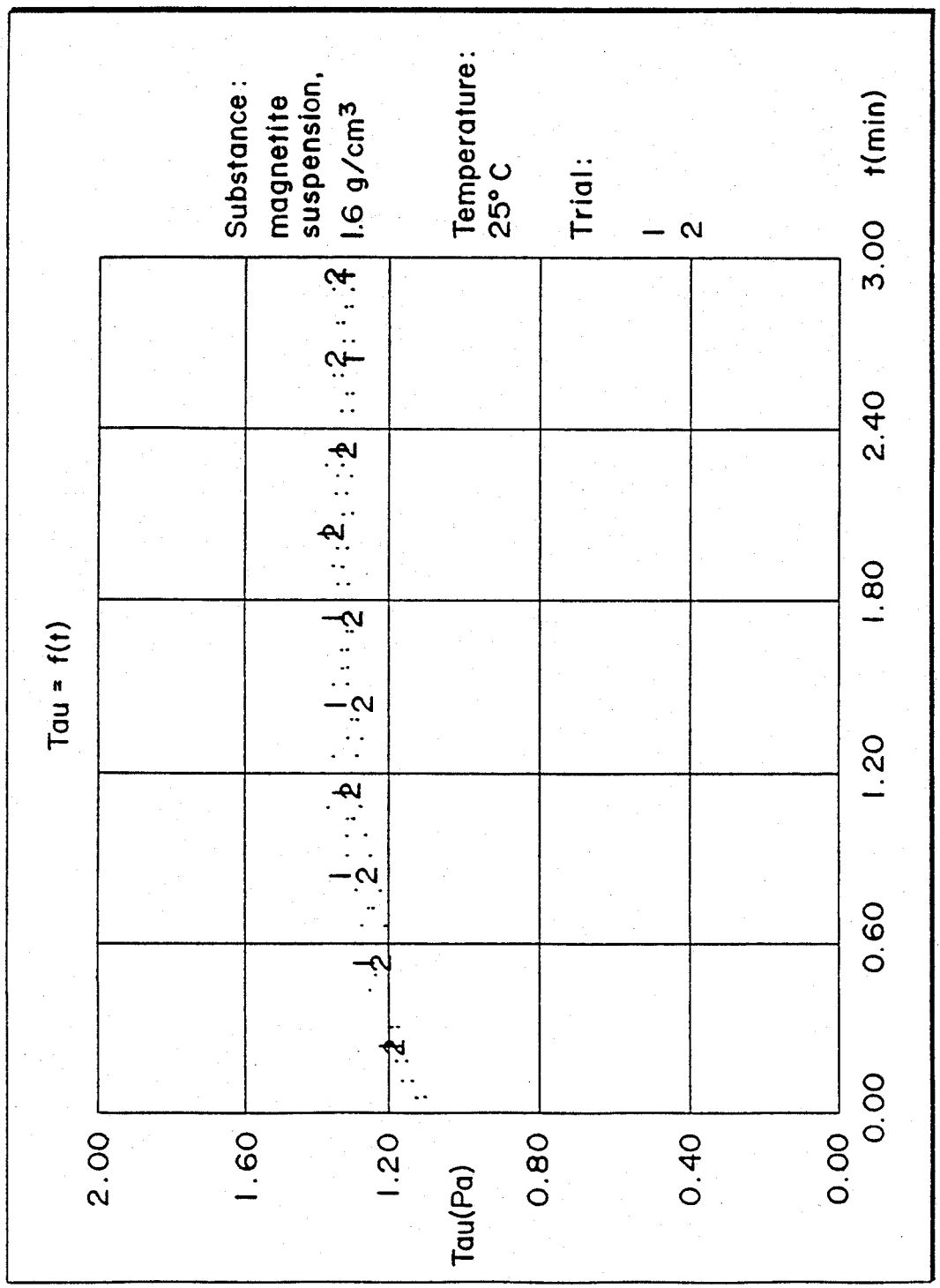
FIG. 8 illustrates stress over time at a bob height.

Experiments were carried out using the double gap concentric cylinder with the bob positioned at 13.5 cm from the bottom of the cup and surrounding the top of the inner cylinder. FIG. 8 reveals that the stress remains constant with time at this bob height. Good reproducibility of results can also be seen.

Figure 9:
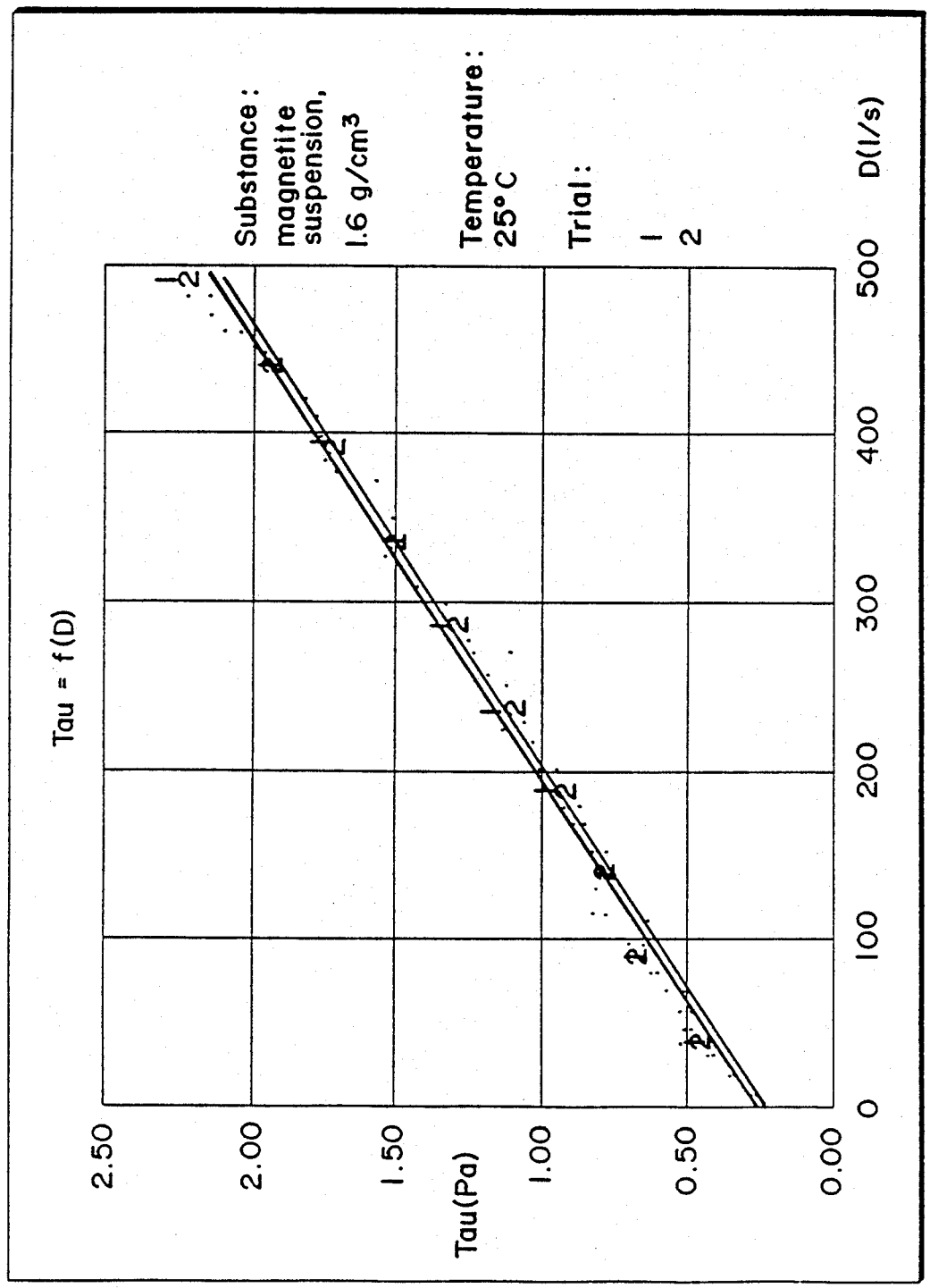
FIG. 9 shows flow curve for a suspension.

This device was used to generate rheological flow curves for a suspension of magnetite, density 1.6 g/cm$^3$. FIG. 9 shows flow curves for the suspension revealing the characteristic Bingham plastic behaviour of magnetite suspensions as well as good reproducibility.

The above results clearly show that:

1. The fixture was accurately calibrated and was used to accurately measure the viscosity of a standard viscosity oil.

2. The magnetite suspensions exhibit the zone settling properties necessary for this procedure.

3. The optimum position of the bob in the cup was determined to be 13.5 cm from the bottom of the cup to the top of the bob for this system.

4. The shear stress was shown to be constant with time for the described fixture arrangement over the time period of interest.

5. Accurate rheological flow curves were generated for a rapidly sedimenting suspension using the described prototype.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. An apparatus for evaluating the rheological properties of sedimenting particle suspensions having a temporary constant density zone comprising:
   (a) means for retaining a sedimenting suspension:
   (b) means suspended in said retaining means and being fully submerged in said sedimenting suspension, said retaining means and said suspended means being capable of being rotated relative to one another, said suspended means having an uninterrupted surface adjacent an uninterrupted surface of the retaining means, said suspended means being permeable to the passage of particles settling in the sedimenting suspension, the suspended means being suspended entirely in the sedimenting suspension in the temporary constant density zone.

2. An apparatus as defined in claim 1 wherein the retaining means is an upright hollow cylinder, closed at the bottom, and being adapted to have the suspended means suspended in the interior thereof through the top region of the cylinder; said suspended means being in the form of a cylinder which has a diameter less than the diameter of the cylindrical retaining means, said suspended means being suspended in the interior of the cylindrical retaining means in a coaxial relationship with the cylindrical retaining means, the retaining means and the suspended means defining therebetween an annular space.

3. An apparatus defined in claim 2 wherein a hollow cylindrical means of diameter less than the cylindrical suspended means is positioned within the greater portion of the interior of the cylindrical suspended means, si hollow inner cylindrical being permeable to particle transmission a the upper end thereof, and being arranged in coaxial relationship with a cylindrical retaining means and the cylindrical suspended means the greater portion of the sidewall of the interior of the cylindrical suspended means, and the greater portion of the exterior sidewall of the inner cylinder means forming therebetween an annular space.

4. An apparatus as defined in claim 3 wherein the cylindrical retaining means is of sufficient height that a sedimenting suspension placed in the interior of the cylindrical retaining means separates for a time into four temporary zones, a supernatant zone, a transition zone adjacent the supernatant zone, a constant density zone adjacent the transition zone, and a consolidation zone at adjacent the transition zone.

5. An apparatus as defined in claim 4 wherein the cylindrical suspended means is suspended in the constant density zone and is rotated relative to the cylindrical retaining means and the inner hollow cylindrical means.

6. An apparatus as defined in claim 4 wherein the cylindrical suspended means is suspended in the constant density zone and the cylindrical retaining means and the inner hollow cylindrical means are rotated relative to the cylindrical suspended means.

7. An apparatus as defined in claim 3 wherein the cylindrical suspended means is suspended by a spider and shaft combination, the spider being permeable to passage of particles settling in the sedimenting suspension, and the shaft mans serving to rotate the cylindrical suspended means relative to the retaining means.

8. An apparatus as defined in claim 3 wherein the cylindrical suspended means is suspended by a spider and shaft combination, the spider being permeable to the passage of particles settling in the sedimenting suspension, the shaft means serving to hold the cylindrical suspended means stationary while the cylindrical retaining means and inner cylinder means are rotated.

9. An apparatus as defined in claim 7 or 8 wherein the apparatus is contained in a temperature control medium.

10. An apparatus as defined in claim 7 or 8 wherein the apparatus is contained in a temperature control medium which is a jacket enveloping a major portion of the apparatus and containing water which is maintained at a constant temperature.

11. A method of evaluating the rheological properties of sedimenting particle suspensions which separate for a period of time into four zones, an uppermost supernatant zone, a transition zone below the supernatant zone, a constant density zone below the transition zone, and a consolidation zone at the bottom of the sedimenting suspension, comprising placing sedimenting suspension in a retaining means and submerging a means in the constant density zone of the suspension, and measuring the rheological properties of the constant density zone by rotating the retaining means and the submerged means relative to one another.

12. A method as defined in claim 11 wherein the retaining means has an uninterrupted surface on at least a part of the surface thereof, and the submerged means has an uninterrupted surface on at least a part thereof, the uninterrupted surface of the retaining means and the submerged means being adjacent to one another.

13. A method as defined in claim 12 wherein a hollow inner means is positioned at one end of the retaining means and has an uninterrupted surface on at least a part thereof adjacent the interior of the uninterrupted surface of the submerged means.

14. A method as defined in claim 13 wherein the retaining means as in the form of a cylindrical cup which is closed at the bottom thereof, the submerged means is in the form of a cylindrical inverted cup, which has a particle porous bottom, and the internal means is in the form of an inverted cylindrical cup which has a particle porous bottom, the opposite end of the inverted cup being connected to the bottom of the retaining means.

15. A method as defined in claim 14 wherein the retaining means and the internal inverted cup means are rotated relative to the submerged means.

* * * * *

UNITED STATES PATENT AND TRADEMARK OFFICE
CERTIFICATE OF CORRECTION

PATENT NO. : 5,056,358
DATED : October 15, 1991
INVENTOR(S) : Janusz S. Laskowski et al.

It is certified that error appears in the above-identified patent and that said Letters Patent is hereby corrected as shown below:

In column 7, claim 3, line 49, please delete "si" and substitute therefor -- said --.

In column 7, claim 3, line 50, please delete "a" and substitute therefor -- at --.

In column 8, claim 7, line 13, please delete "mans" and substitute therefor -- means --.

Signed and Sealed this

Ninth Day of March, 1993

Attest:

STEPHEN G. KUNIN

*Attesting Officer*  Acting Commissioner of Patents and Trademarks

UNITED STATES PATENT AND TRADEMARK OFFICE
CERTIFICATE OF CORRECTION

PATENT NO. : 5,056,358
DATED : October 15, 1991
INVENTOR(S) : Janusz S. Laskowski et al.

It is certified that error appears in the above-identified patent and that said Letters Patent is hereby corrected as shown below:

In column 2, line 46, after "cylindrical", please delete "mean" and substitute therefor -- means --.

In column 7, claim 4, line 63, please delete "at".

Signed and Sealed this

Eighth Day of June, 1993

Attest:

MICHAEL K. KIRK

Attesting Officer

Acting Commissioner of Patents and Trademarks